United States Patent
Koll et al.

(10) Patent No.: US 10,877,620 B2
(45) Date of Patent: *Dec. 29, 2020

(54) MAINTAINING A DISCRETE DATA REPRESENTATION THAT CORRESPONDS TO INFORMATION CONTAINED IN FREE-FORM TEXT

(71) Applicant: MModal IP LLC, Franklin, TN (US)

(72) Inventors: Detlef Koll, Pittsburgh, PA (US); Christopher Scott, Pittsburgh, PA (US); Juergen Fritsch, Pittsburgh, PA (US); Anna Abovyan, Pittsburgh, PA (US); Michael Finke, Pittsburgh, PA (US)

(73) Assignee: MModal IP, LLC, Franklin, TN (US)

( * ) Notice: Subject to any disclaimer, the term of this patent is extended or adjusted under 35 U.S.C. 154(b) by 18 days.

This patent is subject to a terminal disclaimer.

(21) Appl. No.: 16/174,503

(22) Filed: Oct. 30, 2018

(65) Prior Publication Data

US 2019/0065008 A1  Feb. 28, 2019

Related U.S. Application Data

(63) Continuation of application No. 13/965,836, filed on Aug. 13, 2013, now Pat. No. 10,156,956.
(Continued)

(51) Int. Cl.
*G06F 17/24* (2006.01)
*G06F 3/0481* (2013.01)
(Continued)

(52) U.S. Cl.
CPC ............ *G06F 3/0481* (2013.01); *G06F 19/00* (2013.01); *G06F 40/174* (2020.01); *G16H 10/60* (2018.01); *G16H 50/20* (2018.01)

(58) Field of Classification Search
CPC .. G06F 19/345; G06F 19/322; G06F 19/3437; G06F 19/3456; G06F 19/3418;
(Continued)

(56) References Cited

U.S. PATENT DOCUMENTS 5,483,443 A   1/1996 Milstein et al.
6,529,876 B1  3/2003 Dart et al.
(Continued)

FOREIGN PATENT DOCUMENTS

EP   2030196 B1   9/2018
EP   2883203 B1   10/2018
(Continued)

OTHER PUBLICATIONS

"Medical Decision Making and the Marshfield Clinic Scoring Tool FAQ," American College of Emergency Physicians, May 24, 2017, 3 pages [online: https://www.acep.org/administration/reimbursement/reimbursement-faqs/medical-decision-making-and-the-marshfield-clinic-scoring-tool-faq/#sm.000019luk7uslud34somv72pq17x3].
(Continued)

*Primary Examiner* — Di Xiao
(74) *Attorney, Agent, or Firm* — Blueshift IP, LLC; Robert Plotkin

(57) ABSTRACT

A system includes a data record (such as an Electronic Medical Record (EMR)) and a user interface for modifying (e.g., storing data in) the data record. The data record includes both free-form text elements and discrete data elements. The user interface includes user interface elements for receiving free-form text data. In response to receiving free-form text data via the free-form text user interface elements, a suggested action is identified, such as a suggested action to take in connection with one of the discrete data elements of the data record. Output is generated representing the suggested action. A user provides input indi-
(Continued)

cating acceptance or rejection of the suggested action. The suggested action may be performed in response to the user input.

30 Claims, 5 Drawing Sheets

Related U.S. Application Data

(60) Provisional application No. 61/682,748, filed on Aug. 13, 2012.

(51) Int. Cl.
    *G16H 50/20*     (2018.01)
    *G16H 10/60*     (2018.01)
    *G06F 40/174*     (2020.01)
    *G06F 19/00*     (2018.01)

(58) Field of Classification Search
CPC .............. G06F 19/3481; G06F 19/3487; G06F 19/3443; G06F 19/363; G06F 19/325; G06F 19/327; G06F 17/30976; G06F 19/3406; G06F 17/2785; G06F 19/324; G06F 19/328; G06F 19/24; G06F 19/3431; G06F 17/2735; G06F 17/279; G06F 17/289; G06F 17/30; G06F 17/30395; G06F 17/30516; G06F 17/30528; G06F 17/30539; G06F 17/30554; G06F 17/30598; G06F 17/30864; G06F 17/30997; G06F 19/18; G06F 19/20; G06F 19/28; G06F 19/321; G06F 19/326; G06F 19/3412; G06F 19/3425; G06F 19/3493; G06F 11/008; G06F 11/3447; G06F 11/3466; G06F 17/241; G06F 17/27; G06F 17/2755; G06F 17/2765; G06F 17/30663; G06F 17/30675; G06F 17/30867; G06F 17/30905; G06F 19/3462; G06F 19/366; G06F 21/32; G06F 21/52; G06F 21/563; G06F 2201/86; G06F 2201/87; G06F 2221/2101; G06F 2221/2111; G06F 2221/2141; G06F 3/048

See application file for complete search history.

(56) References Cited

U.S. PATENT DOCUMENTS

| | | | |
|---|---|---|---|
| 7,236,968 | B2 | 6/2007 | Seki |
| 7,313,515 | B2 | 12/2007 | Crouch |
| 7,650,628 | B2 | 1/2010 | Zimmerman |
| 7,885,811 | B2 | 2/2011 | Zimmerman |
| 8,452,609 | B2 | 5/2013 | Berg |
| 8,706,521 | B2 | 4/2014 | Ramarajan |
| 8,781,853 | B2 | 7/2014 | Green, III |
| 10,156,956 | B2 | 12/2018 | Koll |
| 10,325,296 | B2 | 6/2019 | Koll |
| 2002/0029161 | A1 | 3/2002 | Brodersen |
| 2003/0074248 | A1 | 4/2003 | Braud |
| 2003/0133156 | A1 | 7/2003 | Cragun |
| 2006/0036472 | A1 | 2/2006 | Crockett |
| 2007/0013968 | A1 | 1/2007 | Ebaugh |
| 2007/0143141 | A1 | 6/2007 | Villasenor et al. |
| 2009/0271218 | A1 | 10/2009 | Mok |
| 2009/0287678 | A1 | 11/2009 | Brown |
| 2010/0100570 | A1 | 4/2010 | Constantin et al. |
| 2010/0299320 | A1* | 11/2010 | Claud ............... G06F 16/332 707/722 |
| 2011/0239146 | A1* | 9/2011 | Dutta ............... G06Q 10/109 715/768 |
| 2011/0295864 | A1* | 12/2011 | Betz ............... G06F 16/38 707/754 |
| 2012/0010900 | A1 | 1/2012 | Kaniadakis |
| 2012/0016690 | A1 | 1/2012 | Ramarajan et al. |
| 2013/0110547 | A1 | 5/2013 | Englund et al. |
| 2013/0226617 | A1 | 8/2013 | Mok |
| 2013/0238330 | A1 | 9/2013 | Casella Dos Santos |
| 2015/0066537 | A1 | 3/2015 | Sheffer et al. |
| 2015/0278449 | A1 | 10/2015 | Laborde |
| 2015/0356198 | A1 | 12/2015 | D'Souza et al. |
| 2015/0356647 | A1 | 12/2015 | Reiser et al. |
| 2016/0093010 | A1 | 3/2016 | Vasiliu-Feltes et al. |
| 2016/0371447 | A1 | 12/2016 | Koman |
| 2017/0068781 | A1 | 3/2017 | Zasowski |
| 2018/0081859 | A1 | 3/2018 | Snider |
| 2018/0276188 | A1 | 9/2018 | Koll |
| 2019/0026436 | A1 | 1/2019 | Bender |

FOREIGN PATENT DOCUMENTS

| | | | |
|---|---|---|---|
| EP | 3571608 | A1 | 11/2019 |
| JP | 4037250 | B2 | 1/2008 |
| JP | 6388864 | B2 | 9/2018 |
| WO | 2009143395 | A1 | 11/2009 |
| WO | 2015079354 | | 6/2015 |
| WO | 2019103930 | | 5/2019 |

OTHER PUBLICATIONS

Advisory Action dated Nov. 21, 2018 in U.S. Appl. No. 14/941,445 of Detlef Koll, filed Nov. 13, 2015, 2 pages.
Anonymous: "DMXzone Universal Form Validator PHP", Sep. 2, 2009, XP055432714, [online: https://www.dmxzone.com/Downloads/Tutorial_FormValidatorPHP_update.zip/FormValidatorPHP_update.pdf].
Centers for Medicare & Medicaid Services, "Medicare Physician Guide: 1995 Documentation Guidelines For Evaluation and Management Services," 1995, 16 pages [online: https://www.cms.gov/Outreach-and-Education/Medicare-Learning-Network-MLN/MLNEdWebGuide/Downloads/95Docguidelines.pdf].
Centers for Medicare & Medicaid Services, "Medicare Physician Guide: 1997 Documentation Guidelines For Evaluation and Management Services ," 1997, 49 pages [online: https://www.cms.gov/Outreach-and-Education/Medicare-Learning-Network-MLN/MLNEdWebGuide/Downloads/97Docguidelines.pdf].
Communication pursuant to Article 94(3) EPC dated Jan. 8, 2019 by the European Patent Office in patent application No. 13809956.9, 5 pages.
Examination Report received in Canadian patent application No. 2,791,292 dated Sep. 19, 2018, 9 pages.
Final Office Action dated Sep. 4, 2018 in U.S. Appl. No. 14/218,220 of Juergen Fritsch, filed Mar. 18, 2014, 46 pages.
Final Rejection dated Oct. 11, 2018 for U.S. Appl. No. 14/941,445 of Detlef Koll, filed Nov. 13, 2015, 16 pages.
James Flanagan, et al. "Defining the Standards for Automated E&M Coding Through Coding Consistency Methodology," Perspectives in Health Information Management, CAC Proceedings; Fall 2008, 7 pages [online: http://perspectives.ahima.org/defining-the-standards-for-automated-earn-coding-through-coding-consistency-methodology/].
Non-Final Office Action dated Sep. 4, 2018 in U.S. Appl. No. 15/839,037 of Detlef Koll, filed Dec. 12, 2017, 22 pages.
Slabodkin Greg, "CMS proposed rulereduces Evaluation andManagement coding burden",Jul. 13, 2018, 4 pages,"https://www.healthdatamanagement.com/news/cms-proposed-rule-reduces-evaluation-and-management-coding-burden?reconf=1".
Stephanie L. Jones "E/M Audit Tool: to be used with AAPC Specialty examinations," 2006 reprinted by American Academy of Professional Coders, 2 pages [online: https://c.ymcdn.com/sites/www.txosteo.org/resource/resmgr/imported/EM%20AuditTool%20from%20Practicum.pdf].
Summons to Attend Oral Proceedings pursuant to Rule 115(1) EPC mailed Oct. 31, 2018, in European Patent Application No. 12802338.9, 8 pages.

(56) References Cited

OTHER PUBLICATIONS

Decision to Refuse European Application dated Oct. 24, 2019 in European Patent Application No. 11748231.5, 19 pages.
Final Rejection dated Nov. 5, 2019 for U.S. Appl. No. 14/941,445 of Detlef Koll, filed Nov. 13, 2015, 19 pages.
Final Rejection dated Nov. 27, 2019 for U.S. Appl. No. 15/872,532 of Gilan El Saadawi, filed Jan. 16, 2018, 33 pages.
First Examination Report dated Oct. 7, 2019 in Indian patent application No. 7449/DELNP/2012, 9 pages.
Petition for Inter Parties Review of U.S. Pat. No. 8,781,829 filed before the Patent Trial and Appeal Board on Dec. 21, 2018 by PetitionerNuance Communications, Inc., 81 pages.
Exhibit 1003 of Petition for Inter Parties Review of U.S. Pat. No. 8,781,829 filed before the Patent Trial and Appeal Board on Dec. 21, 2018 by Petitioner Nuance Communications, Inc., Declaration of Andrew Sears.
Exhibit 1004 of Petition for Inter Parties Review of U.S. Pat. No. 8,781,829 filed before the Patent Trial and Appeal Board on Dec. 21, 2018 by Petitioner Nuance Communications, Inc., Curriculum Vitae of Andrew Sears.
Exhibit 1005 of Petition for Inter Parties Review of U.S. Pat. No. 8,781,829 filed before the Patent Trial and Appeal Board on Dec. 21, 2018 by Petitioner MModal Services Ltd., Michael Freeman Bliss, "Speech Recognition for Health Professionals", Pearson Prentice Hall, pp. 18-24, (2005).
Exhibit 1007 of Petition for Inter Parties Review of U.S. Pat. No. 8,781,829 filed before the Patent Trial and Appeal Board on Dec. 21, 2018 by Petitioner Nuance Communications, Inc., Panzarasa et al., "Technical Solutions for Integrating Clinical Practice Guidelines with Electronic Patient Records", pp. 141-154, (2010).
Exhibit 1009 of Petition for Inter Parties Review of U.S. Pat. No. 8,781,829 filed before the Patent Trial and Appeal Board on Dec. 21, 2018 by Petitioner Nuance Communications, Inc., Joel D. Miller and Elizabeth M. Wenzel, "Recent Developments in SLAB: A Software-Based System for Interactive Spatial Sound Synthesis", Proceedings of 2002, Int'l Conf. on Auditory Display, pp. IDAC02 1-IDAC02 6, Jul. 2-5, 2002.
Exhibit 1010 of Petition for Inter Parties Review of U.S. Pat. No. 8,781,829 filed before the Patent Trial and Appeal Board on Dec. 21, 2018 by Petitioner MModal Services Ltd., JCAHO—Specification Manual for National Implementation of Hospital Core Measures, Version 2.0 (Mar. 1, 2004).
Exhibit 1011 of Petition for Inter Parties Review of U.S. Pat. No. 8,781,829 filed before the Patent Trial and Appeal Board on Dec. 21, 2018 by Petitioner MModal Services Ltd., JCAHO—Introduction and Background.
Exhibit 1012 of Petition for Inter Parties Review of U.S. Pat. No. 8,781,829 filed before the Patent Trial and Appeal Board on Dec. 21, 2018 by Petitioner Nuance Communications, Inc., JCAHO—Using the Specifications Manual for National Implementation of Hospital Core Measures.
Exhibit 1013 of Petition for Inter Parties Review of U.S. Pat. No. 8,412,524 filed before the Patent Trial and Appeal Board on Dec. 21, 2018 by Petitioner Nuance Communications, Inc., W. H. Auden, "Menu Selection and Form Filing", Semantic Organization, Chapter 3, 1970.
Exhibit 1014 of Petition for Inter Parties Review of U.S. Pat. No. 8,781,829 filed before the Patent Trial and Appeal Board on Dec. 21, 2018 by Petitioner MModal Services Ltd., Alan J. Dix et al., "Human-Computer Interaction", 2nd ed., pp. 130-137, (1998).
Exhibit 1015 of Petition for Inter Parties Review of U.S. Pat. No. 8,781,829 filed before the Patent Trial and Appeal Board on Dec. 21, 2018 by Petitioner Nuance Communications, Inc., Frequently Asked Questions: Signature Requirements, Cahaba Government Benefit Administrators (Mar. 2011).
Exhibit 1016 of Petition for Inter Parties Review of U.S. Pat. No. 8,781,829 filed before the Patent Trial and Appeal Board on Dec. 21, 2018 by Petitioner Nuance Communications, Inc., WayBackMachine capture of CDC Website ICD-9-CM classification explanation, available at https://web.archive.org/web/20110430031819/https://www.cdc.gov/nchs/icd/icd9cm.htm (Apr. 30, 2011).
Exhibit 1017 of Petition for Inter Parties Review of U.S. Pat. No. 8,781,829 filed before the Patent Trial and Appeal Board on Dec. 21, 2018 by Petitioner MModal Services Ltd., MModal's Preliminary Claim Construction Disclosure, *MModal Services Ltd v. Nuance Communications, Inc.*, Case No. 1:18-cv-00901-WMR (N.D. Ga. Dec. 3, 2018).
Exhibit 1018 of Petition for Inter Parties Review of U.S. Pat. No. 8,781,829 filed before the Patent Trial and Appeal Board on Dec. 21, 2018 by Petitioner Nuance Communications, Inc., JCAHO Facts, Joint Commission on Accreditation of Healthcare Organizations, (Aug. 1, 2005).
Exhibit 1019 of Petition for Inter Parties Review of U.S. Pat. No. 8,781,829 filed before the Patent Trial and Appeal Board on Dec. 21, 2018 by Petitioner Nuance Communications, Inc., Roe, D. B., & Wilpon, J. G. (Eds.). Voice communication between humans and machines. National Academies Press., pp. 165-198 (1994).
Exhibit 1020 of Petition for Inter Parties Review of U.S. Pat. No. 8,781,829 filed before the Patent Trial and Appeal Board on Dec. 21, 2018 by Petitioner MModal Services Ltd., Win Phillips, "Introduction to Natural Language Processing, Consortium on Cognitive Science Instruction (Apr. 1999)", available at https://web.archive.org/web/20090221020728/http:/www.mind.ilstu.edu/curriculum/protothinker/natural_language_processing.php (Sep. 1, 2006).
Exhibit 1021 of Petition for Inter Parties Review of U.S. Pat. No. 8,781,829 filed before the Patent Trial and Appeal Board on Dec. 21, 2018 by Petitioner Nuance Communications, Inc., Laurence S. Gillick, "A Rapid Match Algorithm for Continuous Speech Recognition", HLT 1990 Proceedings of the Workshop on Speech and Natural Language, pp. 170-172, (Jun. 24, 1990).
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 1-66.
Exhibit 1022 of Petition for Inter Parties Review of U.S. Pat. No. 8,781,829 filed before the Patent Trial and Appeal Board on Dec. 21, 2018 by Petitioner MModal Services Ltd., Declaration of Dr. James Mullins regarding public availability of Panzarasa, pp. 67-110.
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 111-153.
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 154-201.
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 202-243.
Exhibit 1022 of Petition for Inter Parties Review of U.S. Pat. No. 8,781,829 filed before the Patent Trial and Appeal Board on Dec. 21, 2018 by Petitioner MModal Services Ltd., Declaration of Dr. James Mullins regarding public availability of Panzarasa, pp. 244-273 end.
Examiner's Report dated Dec. 20, 2018 in Canadian patent application No. 2,839,266, 4 pages.
International Search Report and Written Opinion received for PCT Patent Application No. PCT/US2018/061517, dated Mar. 7, 2019, 10 pages.
Examiner's Report dated Apr. 15, 2019 in Canadian patent application No. 2,875,584, 4 pages.
Non-Final Rejection dated Jun. 19, 2019 in U.S. Appl. No. 15/872,532 of Gilan El Saadawi, filed Jan. 16, 2018, 54 pages.
Examination Report dated Jun. 18, 2019, in Canadian patent application No. 2,811,942, 6 pages.
Examination Report received in Canadian patent application No. 2,791,292 dated Aug. 2, 2019, 7 pages.

(56) References Cited

OTHER PUBLICATIONS

First Examination Report dated Aug. 29, 2019 in Indian patent application No. 448/MUMNP/2013, 6 pages.
International Search Report and Written Opinion received for PCT Patent Application No. PCT/US2018/013868, dated Jun. 18, 2018, 14 pages.
Non-Final Rejection dated Sep. 16, 2019 for U.S. Appl. No. 15/993,958 of Detlef Koll, filed May 31, 2018, 65 pages.
Arup Sarma et al., "Context-based Speech Recognition Error Detection and Correction," Proceedings of HLT-NAACL 2004: Short Papers, May 2004, 4 pages.
Communication Pursuant to Article 94(3) EPC, dated Jun. 27, 2019, in EPO application No. 14762803.6, 11 pages.
Examiner's Report dated Jun. 27, 2019 in Canadian Patent Application No. 2,881,564, 6 pages.
First Examination Report in Indian patent application No. 2186/MUMNP/2012 dated Jul. 19, 2019, 7 pages.
International Preliminary Report on Patentability, dated Aug. 1, 2019 in International Patent Application No. PCT/US2018/013868, 9 pages.
Non-Final Rejection dated Jul. 22, 2019 in U.S. Appl. No. 14/941,445 of Detlef Koll, filed Nov. 13, 2015, 29 pages.
Summons to Attend Oral Proceedings Pursuant to Rule 115(1) EPC dated Jun. 12, 2019 in European Patent Application No. 11748231.5, 11 pages.
Examiner's Report dated Nov. 29, 2019 in Canadian patent application No. 2,839,266, 4 pages.
First Examination Report dated Dec. 24, 2019, in Indian patent application No. 336/DELNP/2014, 7 pages.
Non-Final Rejection dated Jan. 9, 2020 for U.S. Appl. No. 15/788,522 of Detlef Koll, filed Oct. 19, 2017, 55 pages.
Second Examiner's Report dated May 20, 2020, in Canadian patent application No. 2,875,584, 5 pages.
Non Final Rejection dated Jun. 10, 2020 for U.S. Appl. No. 15/993,958 of Detlef Koll, filed May 31, 2018, 14 pages.
Examination Report received in Canadian patent application No. 2,791,292 dated Mar. 9, 2020, 3 pages.
Final Rejection dated Jul. 14, 2020 for U.S. Appl. No. 15/788,522 of Detlef Koll, filed Oct. 19, 2017, 33 pages.
Final Rejection dated Jul. 21, 2020 in U.S. Appl. No. 15/872,532 of Gilan El Saadawi, filed Jan. 16, 2018, 38 pages.
Final Rejection dated Mar. 16, 2020 for U.S. Appl. No. 15/993,958 of Detlef Koll, filed May 31, 2018, 33 pages.
Non-Final Rejection dated Mar. 6, 2020 in U.S. Appl. No. 14/941,445 of Detlef Koll, filed Nov. 13, 2015, 16 pages.
Examination Report dated Feb. 4, 2020, in Canadian patent application No. 2,904,656, 5 pages.
Summons to Attend Oral Proceedings Pursuant to Rule 115(1) EPC mailed Mar. 24, 2020, by the European Patent Office in patent application No. 13809956.9, 10 pages.
Non Final Rejection dated Apr. 3, 2020 for U.S. Appl. No. 15/872,532 of Gilan El Saadawi, filed Jan. 16, 2018, 22 pages.
Non Final Rejection dated Apr. 6, 2020 for U.S. Appl. No. 15/616,884 of Detlef Koll, filed Jun. 7, 2017, 7 pages.
Non Final Rejection dated May 14, 2020 for U.S. Appl. No. 16/193,443 of Derek L. Nichols, filed Nov. 16, 2018, 64 pages.

* cited by examiner

Family History

The patient's family history is negative for any mental illnesses.

The patient's father died two years ago; he had a history of diabetes and high blood pressure.

The patient's mother currently suffers from high cholesterol and hypertension; otherwise she is in relatively good health.

The patient has one sister who was treated for a malignant neoplasm of the breast.

The patient notes that her uncle had an abdominal aneurysm.

☐ NEGATIVE FOR → Psychological Disorder
☐ FATHER → Deceased
☐ FATHER → Diabetes
☐ FATHER → Hypertension
☐ MOTHER → Heart Disease
☐ MOTHER → Hypertension
☐ MOTHER → Alive
☐ SIBLING → Cancer Apply actions

FIG. 2B

MAINTAINING A DISCRETE DATA REPRESENTATION THAT CORRESPONDS TO INFORMATION CONTAINED IN FREE-FORM TEXT

CROSS-REFERENCE TO RELATED APPLICATIONS

This application is related to the following patents and patent applications, which are hereby incorporated by reference herein:
- U.S. Pat. No. 7,584,103, issued on Sep. 1, 2009, entitled, "Automatic Extraction of Semantic Content and Generation of a Structured Document from Speech";
- U.S. Pat. No. 7,716,040, issued on May 11, 2010, entitled, "Verification of Extracted Facts";
- U.S. patent application Ser. No. 13/025,0501, filed on Feb. 10, 2011, entitled, "Providing Computable Guidance to Relevance Evidence in Questions-Answering Systems";
- U.S. patent application Ser. No. 13/036,841, filed on Feb. 28, 2011, entitled, "Clinical Data Reconciliation as Part of a Report Generation Solution"; and
- U.S. patent application Ser. No. 13/527,347, filed on Jun. 19, 2012, entitled, "Document Extension in Dictation-Based Document Generation Workflow".

BACKGROUND

The clinical documentation systems used in connection with many modern electronic medical records (EMRs) include both user interface elements for entering discrete data into EMRs and user interface elements for entering free-form text into EMRs. Examples of common user interface elements for entering discrete data into EMRs include checkboxes and radio buttons to indicate the presence of absence of problems, complications, conditions of family members, and tests performed during a physical examination; date selection controls to capture the onset or end of certain events (e.g., the date on which pain started, when a family member died, or on which treatment began or ended); and dropdown lists to indicate current and past medications. The most common example of a user interface element for entering free-form text into EMRs is a text field.

Although it might seem that it would be desirable to design clinical documentation systems to include only user interface elements for entering discrete data elements in order to eliminate ambiguity and subjectivity from such data entry, typically it is not possible or desirable to represent all possible inputs using discrete user interface elements, even for narrowly-defined subsets of a clinical document. One reason for this is that discrete user interface elements are not capable of capturing uncommon events, conditionality between multiple observations, uncertainty in observations that cannot accurately be represented by a binary parameter value (e.g., "the patient exhibits signs of X"), and causality. More generally, requiring all EMR data to be entered using discrete UI elements would fail to capture the story of a patient and the thought process of the authoring physician in a way that is both memorable and interpretable by the authoring or other physicians.

As a result, clinical documentation systems typically allow free-form text to be entered into EMRs. For example, it is common for such systems to include a free-form text entry field alongside each logical grouping of discrete user interface elements. For example, a free-form text entry field may be provided for a "History of Present Illness" grouping of discrete user interface elements, another free-form text entry field may be provided for a "Family History" grouping of discrete user interface elements, and yet another free-form text entry field may be provided for a "Physical Examination" grouping of discrete user interface elements.

The resulting graphical user interface includes both user interface elements for receiving discrete data input and user interface elements for receiving free-form text input. As a consequence, the underlying data model into which data received using the graphical user interface is stored is also a hybrid of discrete data and free-form text data.

There are at least two problems with such an EMR system:

(1) Discrete data entry fields tend to be much less user friendly than free-form text entry fields. For example, a typical data entry form for a physical examination may contain hundreds of checkboxes and other discrete data entry user interface elements. It can be difficult and time-consuming to find the right checkboxes to check, in comparison to merely typing or dictating a free-form text description of the same information. As a result, physicians or others who enter data into such an EMR system may either accept reduced productivity and data fidelity by entering data into the discrete data fields, or bypass the discrete data fields and just enter free-form text into the corresponding free-form text fields and thereby forfeit the benefits of the discrete data fields.

(2) It is generally not possible to ensure consistency between the data contained in a free-form text field and data contained in the corresponding discrete data fields. For example, consider the case in which one set of discrete data fields contain fields to capture palliative care instructions for a patient. Associated with such discrete data fields may be a free-form text entry field. If the physician chooses to enter instructions (e.g., a "Do Not Resuscitate" order) into the free-form text entry field and leaves the discrete data fields blank, then the information in the free-form text entry field will not be reflected in the discrete data fields. If the contents of the discrete data fields are used to drive a clinical workflow, then such a workflow will not be triggered if the text entry field contains data but the discrete data fields are empty.

There is, however, substantial value in the discrete data elements, such as for automating common care workflows and for use in decision support processes. One way to address the problems described above is to abstract information contained in free form-text fields, to reconcile the abstracted information with the last known state of the discrete data elements, and to let the user verify the reconciled data state as part of the free-form text input. One drawback of this approach is that to perform reconciliation, decisions may need to be made regarding the appropriate representation of the free-form text data within the discrete data model. Any errors in this process may need to be resolved by the user using a user interface that essentially mirrors or is identical to the user interface that is used for discrete data entry. As a result, the cost of implementing such a system may be substantial if it is implemented as an add-on to an existing third-party EMR system, due to the need to duplicate essential parts of the discrete data entry user interface for use in the reconciliation review process.

SUMMARY

A system includes a data record (such as an Electronic Medical Record (EMR)) and a user interface for modifying (e.g., storing data in) the data record. The data record includes both free-form text elements and discrete data elements. The user interface includes user interface elements for receiving free-form text data. In response to receiving free-form text data via the free-form text user interface elements, a suggested action is identified, such as a suggested action to take in connection with one of the discrete data elements of the data record. Output is generated representing the suggested action. A user provides input indicating acceptance or rejection of the suggested action. The suggested action may be performed in response to the user input.

For example, one embodiment of the present invention is directed to a method performed by at least one computer processor, the method comprising: (A) receiving free-form text via a free-form text user interface element of a user interface; (B) identifying a suggested action to perform in connection with a discrete data element of a data record; (C) providing output representing the suggested action; (D) receiving user input indicating whether the user accepts the suggested action.

Other features and advantages of various aspects and embodiments of the present invention will become apparent from the following description and from the claims.

BRIEF DESCRIPTION OF THE DRAWINGS

FIG. 2B is a concrete diagram of a user interface for receiving user input for updating the EMR of FIG. 1 according to one embodiment of the present invention;

DETAILED DESCRIPTION

Embodiments of the present invention may be used to significantly reduce the integration costs described above. For example, instead of (or in addition to) displaying abstracted concepts identified in free-form text, embodiments of the present invention may use the abstracted concepts to identify logical actions to be performed in the target EMR. Embodiments of the present invention may inform the user of such identified logical actions and, in response to verification from the user, embodiments of the present invention may perform the recommended logical actions automatically.

Figure 1:
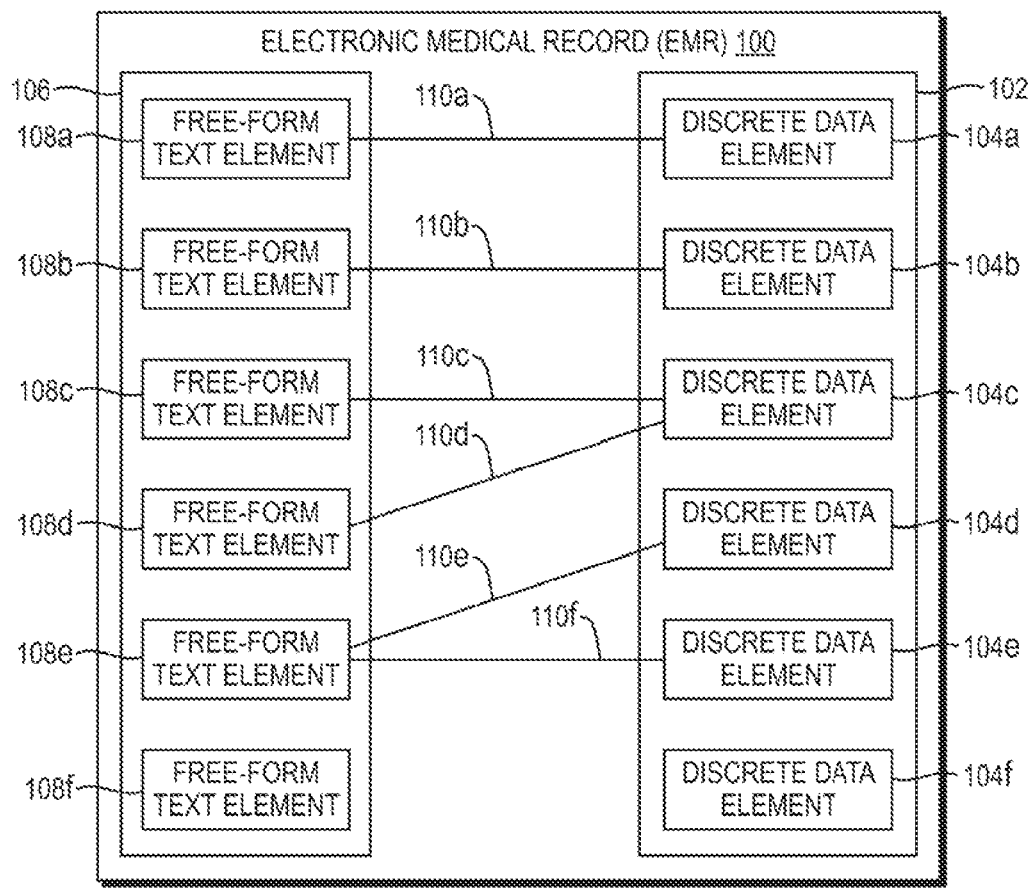
FIG. 1 is a diagram of an electronic medical record (EMR) according to one embodiment of the present invention.

By way of background, consider the example electronic medical record (EMR) 100 illustrated in FIG. 1. The EMR 100 may include both discrete data elements 102 (e.g., fields) and free-form text elements 106 (e.g., fields). Examples of discrete data elements include elements having a finite permissible range of values, such as 0 and 1 (or any equivalent binary range of values, such as "Yes" and "No") or any other finite set of symbols (e.g., {0, 1, 2, 3}, {red, green, blue}, or {alive, deceased}), where a computer is capable of unambiguously determining the meaning of any particular such value. In contrast, a free-form text element may contain any text, such as text input by a human in a natural language, whether or not a computer is capable of unambiguously determining the meaning of such text.

Particular discrete data elements in the EMR 100 may be associated with particular free-form text elements in the EMR 100. In the particular example of FIG. 1:

Discrete data element 104a is associated with text element 108a, as illustrated by association 110a.

Discrete data element 104b is associated with text element 108b, as illustrated by association 110b.

Discrete data element 104c is associated with text elements 108c and 108d, as illustrated by associations 110c and 110d, respectively.

Discrete data elements 104d and 104e are associated with text element 108e, as illustrated by associations 110e and 110f, respectively.

Discrete data element 104f is not associated with any of the text elements 106.

Text element 108f is not associated with any of the discrete data elements 102.

As these examples illustrate, a single one of the discrete data elements 102 in the EMR 100 may be associated with zero, one, or more of the text elements in the EMR 100, and a single one of the text elements in the EMR 100 may be associated with zero, one, or more of the discrete data elements 102 in the EMR 100. The particular associations shown in FIG. 1 are merely examples for purposes of illustration. In practice, a single EMR may include hundreds or more of discrete data elements and text elements, which may have any kind and number of associations with each other.

In general, the associations 110a-f represent a degree of semantic similarity between the associated elements, and/or an influence of the content of associated elements on each other. For example, the association 110a between discrete data element 104a and the text element 108a may indicate that both elements 104a and 108a contain, or are designed to contain, data representing the presence or absence of foot pain in the patient represented by the EMR 100. Further examples of the associations 110a-f will be provided below.

Some or all of the associations 110a-f may be expressly represented and stored as data within the EMR 100. Some or all of the associations 110a-f may, however, not be stored as data within the EMR 100, or anywhere else. Instead, as will become apparent from the description below, embodiments of the present invention may identify some or all of the relationships dynamically and without storing data representing such relationships within the EMR 100. In fact, although the associations 110a-f are shown as fixed in FIG. 1, this is merely an example and does not constitute a limitation of the present invention. For example, embodiments of the present invention may dynamically identify an association between one of the text elements 106 and one or more of the discrete data elements 102 based, at least in part, on the contents of the text element at a particular time. As the contents of the text element change, embodiments of the present invention may identify different associations between the text element and various ones of the discrete data elements 102. The examples describe below will illustrate this ability of embodiments of the present invention to dynamically associate text elements with discrete data elements in response to the contents of such text elements.

Figure 2A:
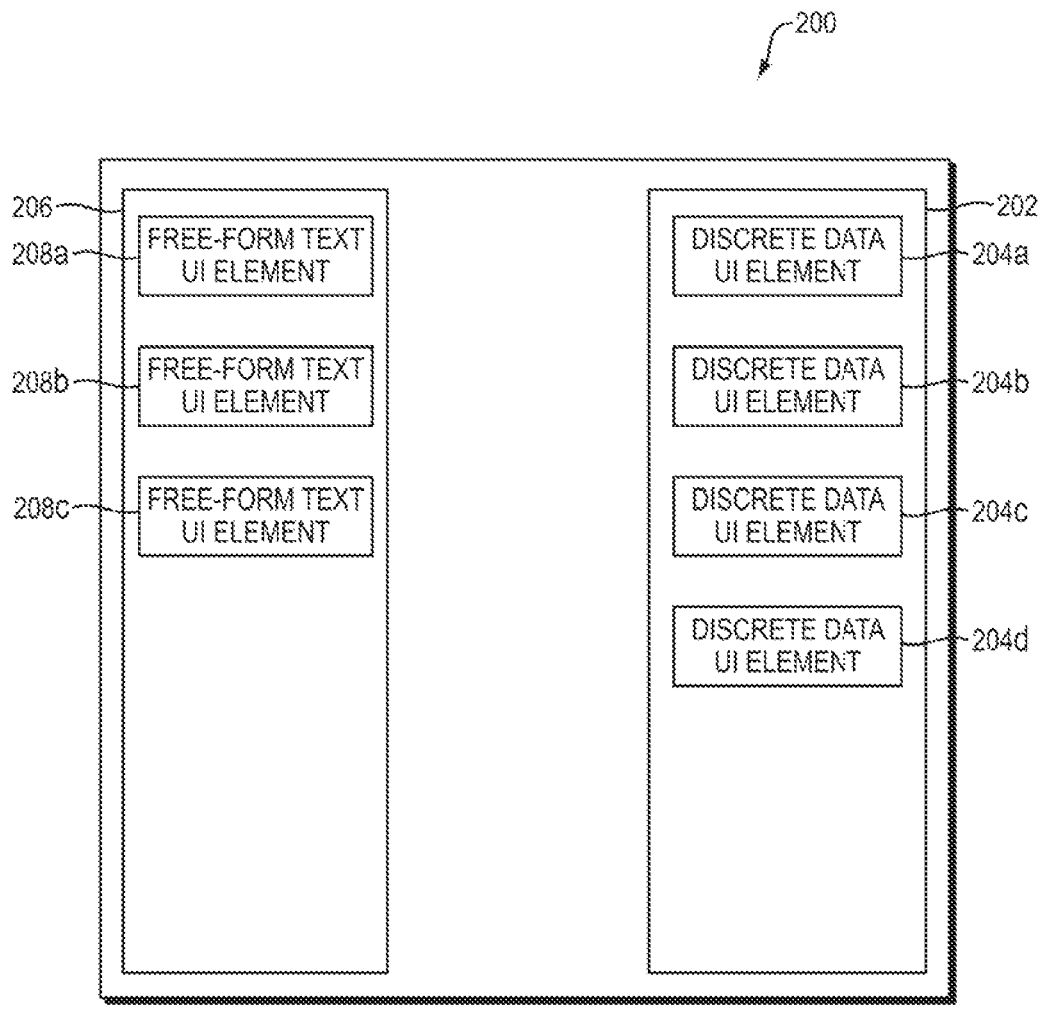
FIG. 2A is an abstract diagram of a user interface for receiving user input for updating the EMR of FIG. 1 according to one embodiment of the present invention.

Now consider the abstract user interface 200 shown in FIG. 2A. FIG. 2A merely shows certain abstract features of the user interface 200 for purposes of illustration. In particular, the user interface 200 includes both discrete data user interface (UI) elements 202 and free-form text UI elements 206. Examples of the discrete data UI elements 202 include checkboxes, radio buttons, dropdown lists, and menus. Examples of free-form text UI elements 206 include single-line text fields, multi-line text fields, including fields having advanced text editing features such as the ability to apply formatting (e.g., font sizes, bold, italics, underline, superscript, subscript, etc.) to text.

Although the user interface 200 may include any number of discrete data UI elements 202 and any number of free-form text UI elements 206, for purposes of example the user interface 200 is shown in FIG. 2A as containing four discrete data UI elements 204a-d and three free-form text UI elements 208a-c. In practice, a user interface 200 for entering data into an EMR may include hundreds of discrete data and free-form text UI elements, arranged in a complex layout, in which the discrete data and free-form text UI elements may span multiple pages or tabs, such that not all of such UI elements may be visible to the user at once.

Discrete data UI elements 202 in the user interface 200 may be mapped to (associated with) zero, one, or more corresponding discrete data elements 102 in the EMR 100 of FIG. 1. Similarly, free-form text UI elements 206 in the user interface 200 may be mapped to (associated with) zero, one, or more corresponding free-form text elements 106 in the EMR 100 of FIG. 1. Although not shown in FIG. 1 or 2A, data representing such mappings may be stored. Such mappings may be one-to-one, one-to-many, or many-to-one. When a user provides input to one of the UI elements 204a-d or 208a-c in the user interface 200 of FIG. 2A, such input may be copied into, or otherwise used to generate values which are stored into, the associated element(s) in the EMR 100 of FIG. 1. For example, if free-form text UI element 208a in the user interface 200 of FIG. 2A is associated with free-form text element 108a in the EMR 100 of FIG. 1, and the user types "John Smith" into the free-form text UI element 208a, the text "John Smith" may be stored in the free-form text element 108a. As another example, if discrete data UI element 204a is a checkbox which is associated with discrete data element 104a in the EMR 100 of FIG. 1, and the user marks the checkbox as checked, then a value of "checked," "yes," "1," or a similar value may be stored in the discrete data element 104a.

In practice, user interface elements 208a-c and 204a-d in the user interface 200 may be organized hierarchically to reflect the structure of a clinical document, such as by grouping various ones of the text UI elements 208a-c and the discrete data UI elements 204a-d into a "Cardiovascular" category, which may itself be one of many groups of UI elements within a "Review of Systems" category. Such a hierarchical grouping establishes a structure indicating which discrete data elements could be associated with particular free-form text elements, and indicating which discrete data elements cannot be associated with particular free-form text elements because they fall within unrelated clinical categories. Content entered into a free-form text UI element within a particular category may be associated with a discrete data UI element within the same category. Certain information entered into a free-form text UI element may, however, not be associated with any discrete data UI element.

Just as the elements 102 and 106 in the EMR 100 of FIG. 1 may have associations 110a-f with each other, elements 202 and 206 in the user interface 200 of FIG. 2A may have associations with each other. Such associations are not shown in FIG. 2A for ease of illustration. Associations between discrete data UI elements 202 and free-form text UI elements 206 in the user interface 200 of FIG. 2A may be implied from the associations 110a-f between the discrete data elements 102 and free-form text elements 106 of the EMR 100 of FIG. 1. For example, assume that:

discrete data UI element 204a in the user interface 200 of FIG. 2A is mapped to the discrete data element 104a in the EMR 100 of FIG. 1;

free-form text UI element 208a in the user interface 200 of FIG. 2A is mapped to the free-form text element 108a in the EMR 100 of FIG. 1; and discrete data element 104a in the EMR 100 of FIG. 1 is associated with free-form text element 108a.

In this case, an association between discrete data UI element 204a and free-form text UI element 208a may be implied from the facts above.

Some or all of the free-form text UI elements 206 in the user interface 200 of FIG. 2A may not be associated (explicitly or implicitly) with any of the discrete data UI elements 202. For example, free-form text UI element 208a may not be associated with any of the discrete data UI elements 204a-d. As will be described in more detail below, however, embodiments of the present invention may be used to enable text that is entered into the free-form text UI element 208a of FIG. 2A to be used to update the values of one or more of the discrete data elements 102 in the EMR 100 of FIG. 1, whether or not the free-form text UI element 208a is associated with any of the discrete data UI elements 202 in the user interface of FIG. 2A. In fact, the user interface 200 need not include any of the discrete data UI elements 202. In particular, the user interface 200 may not include any discrete data elements that are mapped to elements 102 or 106 in the EMR 100.

For example, referring to FIG. 2B, an example is shown of a particular user interface 250 that may be used in connection with embodiments of the present invention. The user interface 250 includes only a single UI element that is mapped to an element of the EMR 100, namely a single free-form text entry field 252 that is mapped to one of the free-form text elements 106 in the EMR 100. (Assume for purposes of example that field 252 in the user interface of FIG. 2B is mapped to free-form text element 108a in the EMR 100 of FIG. 1.) Note that the user interface 250 of FIG. 2B does not include any discrete data UI elements that are mapped to elements 102 or 106 of the EMR 100. As a result, and as will be described in more detail below, embodiments of the present invention use the free-form text that is entered into free-form text entry field 252 to update discrete data elements 102 in the EMR 100 indirectly, by generating suggested actions for updating the discrete data elements 102 based on the contents of the free-form text entry field 252 together with the current state of data elements 102, and performing the suggested actions only if, and in response to, user input confirming that such actions should be performed.

Figure 3:
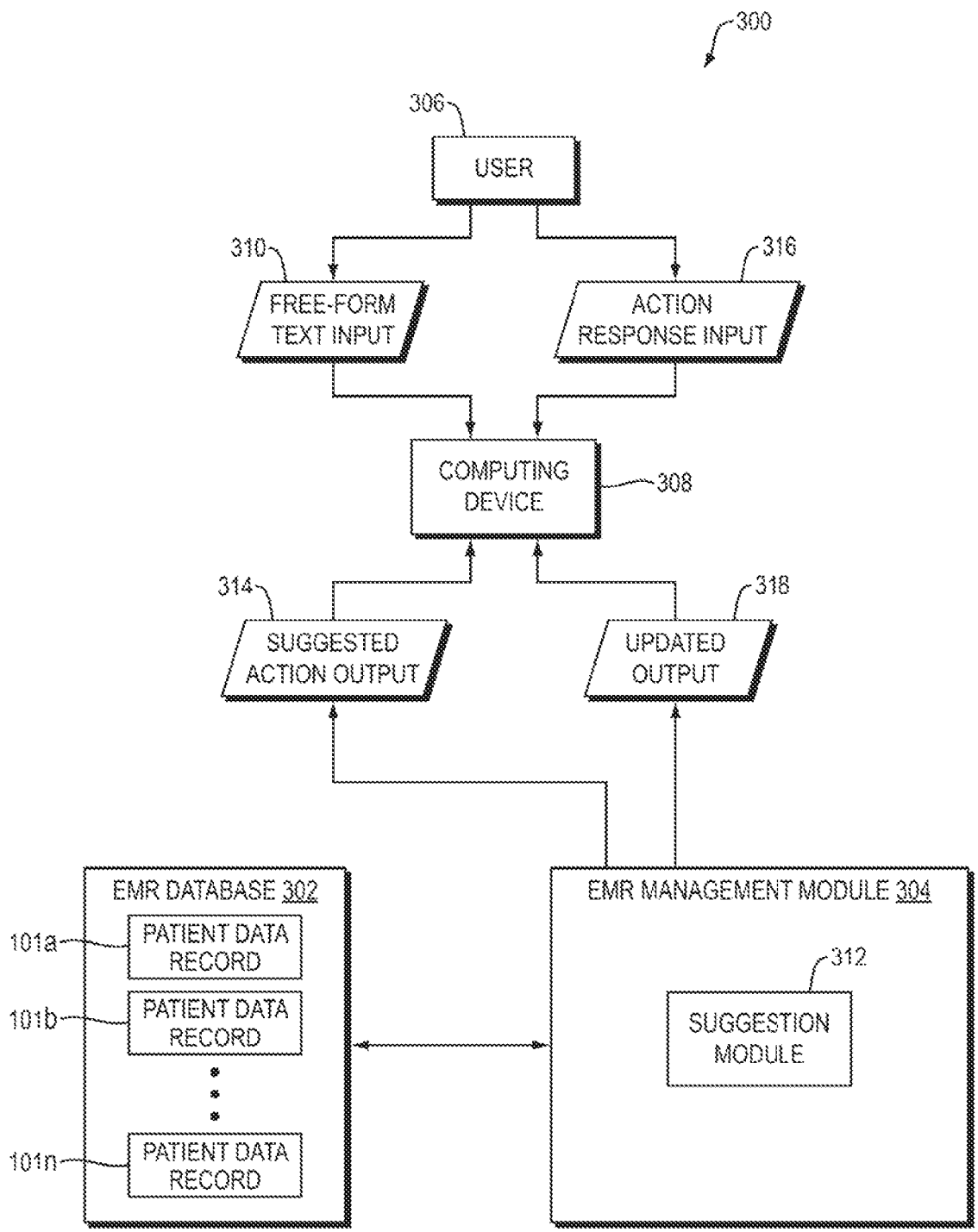
FIG. 3 is a dataflow diagram of a system for updating discrete data elements in the EMR of FIG. 1 based on free-form text provided by a user into the user interfaces of FIGS. 2A-2B.
Figure 4:
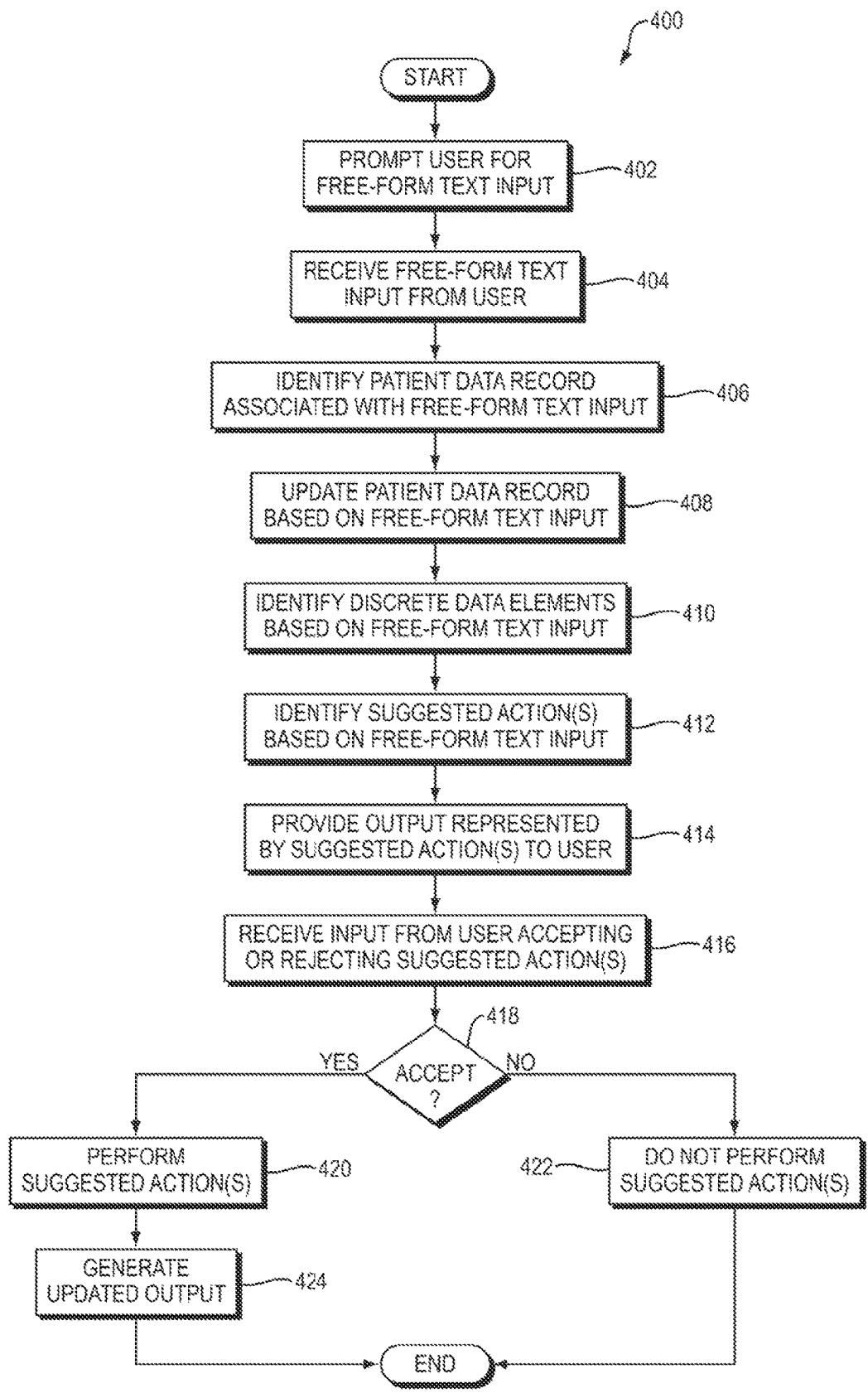
FIG. 4 is a flowchart of a method performed by the system of FIG. 3 according to one embodiment of the present invention.

Certain particular embodiments of the present invention will now be described. Referring to FIG. 3, a dataflow diagram is shown of a system 300 for performing actions on discrete data elements of the EMR 100 according to one embodiment of the present invention. Referring to FIG. 4, a flowchart is shown of a method 400 performed by the system 300 of FIG. 3 according to one embodiment of the present invention.

The system 300 includes an electronic medical record (EMR) database 302, which includes a plurality of patient data records 101a-n (where n may be any number). Each of the patient data records 101a-n may include free-form text elements having associations with discrete data elements, in the manner described above with respect to the patient data record 101a of FIG. 1. The system 300 also includes an EMR management module 304 which may perform any operation on the EMR database 302, such as creating new patient data records, deleting existing patient data records, and updating the contents of existing patient data records. Because an EMR may include one or more patient data records, any reference herein to operations performed on patient data records should be understood to constitute operations that are performed on EMRS. Although the EMR management module 304 is shown as a single component in FIG. 3 for ease of illustration, in practice the EMR management module 304 may be implemented in other ways, such as an add-on or plug-in to an existing EMR system, or as a component that communicates with an existing EMR system to perform the functions disclosed herein.

The system 300 also includes a user 306 and a computing device 308. The computing device 308 receives input from and provides output to the computing device 308 using any suitable I/O device(s). The computing device 308 may be any kind of computing device, such as a desktop computer, laptop computer, tablet computer, or smartphone. The computing device 308 may provide output to and receive input from the EMR management module 304. The user 306, computing device 308, and EMR management module 304 may communicate with each other via a direct connection or via any type of network, such as the public Internet or a private intranet.

The computing device 308 may display, to the user 306, a user interface containing at least one free-form text UI element, or otherwise prompt or enable the user 306 to provide free-form text input (FIG. 4, operation 402). For example, the computing device 308 may display to the user 306 a user interface of the kind shown in FIG. 2B, in which the free-form text field 252 enables the user to provide free-form text input, such as by speaking and/or typing such input. As another example, the computing device 308 may provide a voice prompt, such as "Describe the patient encounter," in response to which the user 306 may provide free-form voice input.

Regardless of the manner in which the computing device 308 enables the user 306 to provide free-form text input, the user 306 may provide such free-form text input 310 to the computing device 308, which receives the input 310 (FIG. 4, operation 404). In the example of FIG. 2B, the user 306 has provided the input 310 by speaking (e.g., into a handheld voice recorder, smartphone, or other device having a microphone or other audio capture component), in response to which the system 300 has transcribed the user's speech (using one or both of an automatic speech recognition (ASR) engine and a human transcriptionist). The computing device has then displayed the resulting transcript within the free-form text field 252.

The EMR management module 304 may generate and/or receive the free-form text input 310. For example, the computing device 308 may provide the free-form text input 310 to the EMR management module 304. As another example, the computing device 308 may receive the free-form text input 310, such as in the form of an audio signal representing speech of the user 306, and transcribe the input 310 to produce a transcript of the input 310, and then provide the transcript to the EMR management module 304. As another example, the computing device 308 may provide the free-form text input 310 in the form of an audio signal representing speech of the user 306 to the EMR management module 304, which may then transcribe the input 310 to produce a transcript of the input 310. In these and other cases, the EMR management module obtains text representing the free-form text input 310 of the user 306, such as the text shown in the free-form text input field 252 of the user interface 250 of FIG. 2B.

If the free-form text input 310 is in the form of an audio signal, the EMR management module 304 may receive the audio signal, a transcript thereof, or both. Any reference herein to the free-form text input 310 should be understood to refer to an audio signal, text and/or other data representing such an audio signal (such as a transcript of the audio signal), or a combination thereof.

The EMR management module 304 may identify a patient data record associated with the free-form text input 310 in the EMR database 302 (FIG. 4, operation 406) and update the identified patient data record based on the free-form text input 310 (FIG. 4, operation 408). The EMR management module 304 may identify the patient data record associated with the free-form text input 310 in any of a variety of ways. For example, the user 306 may (e.g., before providing the free-form text input 310), provide other input (not shown) which identifies the patient who is the subject of the free-form text input 310. Such a patient identifier may be used to identify a corresponding patient data record in the EMR database 302. Assume for purposes of example that the identified patient data record is patient data record 101a.

The EMR management module 304 may update the identified patient data record 101a based on the free-form text input 310 in any of a variety of ways. For example, the EMR management module 304 may identify a free-form text field corresponding to the free-form text input 310 in the identified patient data record 101a, and store the free-form text input 310 in the identified field or otherwise update the identified field based on the free-form text input 310.

The EMR management module 304 includes a suggestion module 312, which identifies one or more discrete data elements in the identified patient data record 101a based on the free-form text input 310 (FIG. 4, operation 410), and which identifies one or more suggested actions to take in connection with the identified discrete data element(s) (FIG. 4, operation 412). Although the suggestion module 312 may identify more than one discrete data element in operation 410 and more than one suggested action in operation 412, the following description will refer to "the identified discrete data element" and "the suggested action" in the singular merely for ease of explanation. Any such references should be understood to refer to one or more identified discrete data elements and one or more suggested actions, respectively.

The suggestion module 312 may identify the discrete data element in operation 410 in any of a variety of ways. For example, as mentioned above, the free-form text UI element (e.g., free-form text field 252) into which the user 306 inputs the free-form text input 310 may be associated with a discrete data element. The suggestion module 312 may identify the discrete data element associated with the free-form text input 310 in operation 410 by identifying the discrete data element that is associated with the free-form text UI element into which the user 306 inputs the free-form text input 310. Alternatively, and as will be described in more detail below, the suggestion module 312 may identify the discrete data element associated with the free-form text input 310 in operation 410 dynamically, i.e., without relying on any predetermined association between free-form text elements and discrete data elements.

The suggestion module 312 may identify any of a variety of suggested actions to take in connection with the identified discrete data element. For example, the suggested action may include storing a specified value in the identified discrete data element, removing the current value from the identified discrete data element, replacing the current value of the identified discrete data element with a specified value, and performing a specified operation on the current value of the identified discrete data element to produce a new value of the identified discrete data element.

The suggestion module 312 may identify the suggested action 314 in any of a variety of ways. For example, the suggestion module 312 may periodically submit some or all of the text in the text entry field 252 to a natural language understanding (NLU) service that abstracts information from the text in the text entry field 252 into one or more concepts. The term "concept," as used herein, may include, for example, one or more characteristics of the patient represented by the patient data record 101a, such as whether the patient represented by the patient data record 101a has or has had a particular medical condition, is taking or has taken a particular medication, or has been provided with particular medical treatment. For generally, the term "concept" may include any fact related to the patient represented by the patient data record 101a.

The suggestion module 312 may use the resulting abstracted concepts to determine the suggested action(s) 314 to take in connection with the target patient data record 101a to cause the target patient data record 101a to reflect the abstracted concepts. For example, the suggestion module 312 may determine whether one or more of the resulting abstracted concepts is inconsistent with one or more of the discrete data elements in the patient data record 101a. For example, if one of the abstracted concepts indicates that the patient represented by the patient data record 101a does not have a psychological disorder and one of the discrete data elements in the patient data record 101a indicates that the patient represented by the patient data record 101a does have a psychological disorder, the suggestion module 312 may conclude that the abstracted concept is inconsistent with the discrete data element. If and in response to determining that one or more of the resulting abstracted concepts is inconsistent with one or more of the discrete data elements in the patient data record 101a, the suggestion module 312 may suggest an action that will cause the one or more discrete data elements to become consistent with the one or more abstracted concepts, such as modifying one or more values of one or more discrete data elements to produce one or more modified values of the one or more discrete data elements. For example, the suggestion module 312 may suggest changing the state of the "psychological disorder" discrete data element from "true" to "false."

As described above, the suggestion module 312 may identify the suggested action 314 based at least in part on the free-form text input 310 received from the user 306. The suggestion module 312 may identify the suggested action 314 based on data in addition to the free-form text input 310, such as data contained in the discrete data elements in the patient data record 101a and in the EMR database 302 more generally. For example, if the free-form text input 310 states, "discontinue all beta blockers," and the patient data record 101a includes a discrete data element representing the medication of "Atenolol," then the suggestion module 312 may identify "Discontinue Atenolol" as the suggested action 314. Generating such a suggested action 314 requires the suggestion module to understand that Atenolol is a type of beta blocker and to combine/reconcile the discrete data already contained within the patient data record 101a with the received free-form text input 310.

The suggestion module 312 may provide output 314 representing the suggested action to the user 306 (FIG. 4, operation 414). The output 314 may be received by the computing device 308 and manifested to the user 306 in any of a variety of ways, such as by generating visual and/or auditory output representing the suggested action. FIG. 2B shows various examples of the output 314, in the form of suggested action output 254. In this example, the suggested action output 254 indicates that the suggestion module 312 suggests:

storing an indication in the patient data record 101a that the patient represented by the patient data record 101a is negative for the ailment of "Psychological Disorder," such as by storing a value of "false" in a "Psychological Disorder" discrete data element in the patient data record 101a;

storing an indication in the patient data record 101a that the father of the patient represented by the patient data record 101a is deceased, such as by storing a value of "deceased" in a discrete data element in the patient data record 101a which indicates whether the patient's father is alive or deceased;

storing an indication in the patient data record 101a that the father of the patient represented by the patient data record 101a has diabetes, such as by storing a value of "true" in a discrete data element in the patient data record 101a which indicates whether the patient's father has diabetes;

storing an indication in the patient data record 101a that the father of the patient represented by the patient data record 101a has hypertension, such as by storing a value of "true" in a discrete data element in the patient data record 101a which indicates whether the patient's father has hypertension;

storing an indication in the patient data record 101a that the mother of the patient represented by the patient data record 101a has heart disease, such as by storing a value of "true" in a discrete data element in the patient data record 101a which indicates whether the patient's mother has heart disease;

storing an indication in the patient data record 101a that the mother of the patient represented by the patient data record 101a has hypertension, such as by storing a value of "true" in a discrete data element in the patient data record 101a which indicates whether the patient's mother has hypertension;

storing an indication in the patient data record 101a that the mother of the patient represented by the patient data record 101a is alive, such as by storing a value of "alive" in a discrete data element in the patient data record 101a which indicates whether the patient's mother is alive or deceased; and storing an indication in the patient data record 101a that a sibling of the patient represented by the patient data record 101a has cancer, such as by storing a value of "cancer" in a current conditions list of the patient's sibling in the patient data record 101a.

It can be seen from FIG. 2B that the suggestion module 312 generated the suggested action of changing the state of the "Psychological Disorder" discrete data element in the patient data record 101a to "negative" based on the following text in the text area 252: "The patient's family history is negative for any mental illnesses." It can be seen that the other actions suggested in the region 254 were generated similarly based on text in the text area 252.

The output 314 representing the action suggested by the suggestion module 312 may take other forms in addition to or instead of the form shown in FIG. 2B. For example, although the user interface 250 of FIG. 2B does not contain any discrete data UI elements, such elements may be included within the user interface 250. For example, a checkbox labeled "Psychological Disorder" may be added to the user interface 250. The system 300 may provide output 314 representing a suggestion to mark the patient as negative for a psychological disorder by providing output in connection with the checkbox, such as one or more of the following:

changing the state of the checkbox to reflect the outcome of performing the suggested action, such as changing the state of the checkbox to unchecked, or leaving it as unchecked if it is already unchecked, so that the visual state of the checkbox corresponds to the outcome of performing the suggested action 314;

visually emphasizing the checkbox, such as by changing its color, displaying a circle or other shape around it, or causing it to blink; and displaying an instruction in connection with (e.g., near) the checkbox to modify a state of the checkbox, such as an instruction stating, "Leave this checkbox unchecked to indicate that the patient is negative for a psychological disorder" or "Uncheck this checkbox to indicate that the patient is negative for a psychological disorder."

The user 306 may provide response input 316 to the computing device 308 (FIG. 4, operation 416). The response input 316 may indicate whether the user 306 accepts or rejects the suggested action 314. (If the suggested action 314 includes more than one suggested action, then the response input 316 may include separate response input for each such suggested action, or a single input indicating whether the user 306 accepts or rejects all such actions.) The computing device 308 may provide the response input 316 to the EMR management module 304.

The response input 316 may take any of a variety of forms. For example, referring to FIG. 2B, the user interface 250 includes an "Apply Actions" button 256. The user 306 may provide the response input 316 by clicking on the "Apply Actions" button 256 to indicate that the user 306 wishes for the system 300 to perform the suggested actions 314 (i.e., the actions described in area 254). If the user 306 does not wish for the system 300 to perform the suggested actions 314, then the user 306 may not click on the "Apply Actions" button 256.

As another example, if the user interface 250 includes discrete data UI elements, the user 306 may provide the response input 316 by providing input to such elements and/or by declining to provide input to such elements. For example, if the user interface 250 includes a "Psychological Disorder" checkbox, and the system 300 has marked that checkbox as unchecked, then the user 306 may provide response input 316 indicating acceptance of the suggested action 314 by leaving the state of the checkbox as unchecked, or provide response input 316 indicating rejection of the suggested action by changing the state of the checkbox to checked. Conversely, the user 306 may indicate acceptance of the suggested action 314 by changing the state of a discrete data UI element (e.g., by changing the state of a "Father Deceased" checkbox from unchecked to checked), and indicate rejection of the suggested action by leaving the state of the discrete data UI element unchanged.

The suggestion module 312 determines whether the response input 316 indicates that the user 306 accepts the suggested action 314 (FIG. 4, operation 418). If the suggestion module 312 determines that the response input 316 indicates that the user 306 accepts the suggested action 314, then the suggestion module 312 performs the suggested action 314 (FIG. 4, operation 420). Performing the suggested action 314 may include changing the state(s) of one or more discrete data elements in the patient data record 101a, in the manner suggested by the suggested action 314. For example, performing the suggested actions specified in the region 254 of FIG. 2B may include changing the state of a "Psychological Disorder" discrete data element in the patient data record 101a to "negative."

The EMR management module 304 may generate updated output 318 reflecting the state of the patient data record 101a that resulted from performing the suggested action 314 (FIG. 4, operation 424). The computing device 308 may display or otherwise manifest the updated output 318 to the user 306, such as by changing the state of a discrete data UI element in the user interface 250 to reflect the state of an associated discrete data element in the patient data record 101a that was updated by the performance of the suggested action 314. For example, in response to changing the state of the "Psychological Disorder" discrete data element in the patient data record 101a to "negative," the EMR management module 304 may generate updated output 318 containing data representing the negative state of the "Psychological Disorder" discrete data element. The computing device 308 may render such output by, for example, changing the state of a "Psychological Disorder" checkbox in the user interface 250 to be unchecked. In this way, the system 300 informs the user 306 of the effects of performing the suggested action 314.

If the suggestion module 312 determines that the response input 316 indicates that the user 306 does not accept the suggested action 314, then the suggestion module 312 does not perform the suggested action 314 (FIG. 4, operation 422).

In the examples provided above, the suggestion module 312 provides at most one suggested action in connection with any particular discrete data element in the patient data record 101a. This is merely an example, however, and does not constitute a limitation of the present invention. The suggestion module 312 may, for example, generate multiple suggested actions in connection with a single discrete data element in the patient data record 101a, including multiple suggested actions which have inconsistent outcomes (e.g., a suggestion to change the state of a discrete data element to "true" and a suggestion to change the state of the discrete data element to "false"). For example, consider a situation in which a free-form text UI element contains the text, "Nodules in left lower lobe suggestive of cancer, but there are no clear indications that would make such a diagnosis possible at this time. Recommend follow up biopsy." The suggestion module may, based on such free-form text, identify any one or more of the following actions: "Add breast cancer to problem list," "Remove breast cancer from problem list," and "Create order for biopsy of lung tissue." In this example, the information contained in the free-form text UI element was ambiguous. In response to such ambiguity, the suggestion module 312 generated two alternative and mutually-exclusive suggested actions ("Add breast cancer to problem list" and "Remove breast cancer from problem list"), thereby making it easier for the user 306 (e.g., physician) to accept one of these two suggested actions even though the system 300 did not determined which of the two suggested actions is represented by the free-form text. Furthermore, in this example the system 300 has generated an additional suggested action ("Create order for biopsy of lung tissue") that is not part of the clinical report itself, but that is a logical next step, given the contents of the free-form text UI element.

As the preceding example further illustrates, embodiments of the present invention are not limited to making suggestions to perform actions on user interface elements. Embodiments of the present invention may make suggestions to directly modify the contents of an EMR (e.g., "Add breast cancer to problem list"). As another example, embodiments of the present invention may make suggestions to perform actions other than modifying the contents of an EMR, such as suggestions to trigger a workflow (e.g., "Create order for biopsy of lung tissue").

Consider another example in which a free-form text UI element contains the text, "Patient recently started to take Celexa against his depressions." The suggestion module 312 may, based on such free-form text, identify the following suggested action: "Add Celexa to the list of current medications." Such a suggested action may not be sufficiently defined to enable the action to be performed fully automatically. For example, the suggested action may lack necessary information, such as start date and dosage. The generation of such a suggested action may, however, be supplemented by automatically displaying the medication list of the patient data record 101a to the user 306 (e.g., physician) to facilitate the process of the user 306 adding Celexa to the medication list. As another example, the EMR management module 304 may add Celexa to the medication list in the patient data record 101a automatically and enter any additional available data automatically, and then enable the user 306 to enter any remaining necessary data manually. Such a process may make it easier for the user 306 to add a medication to the medication list even though the process does not perform all steps of adding the medication to the medication list automatically.

Embodiments of the present invention have a variety of advantages. For example, as described above, conventional EMR systems often include both free-form text elements and discrete data elements for representing the same information. As a result, it is common for the data in such redundant elements to be inconsistent with each other. For example, a "Psychological Disorder" free-form text field in an EMR may include the text, "Patient suffers from schizophrenia," while a "Psychological Disorder" discrete data element in the same EMR may include the value "false." Such inconsistencies can be particularly difficult to detect, prevent, and eliminate in modern EMR systems, particularly because a single EMR may include hundreds of fields, and because the user interface elements representing those fields (e.g., text fields and checkboxes) may be not be displayed to the user in a manner which makes clear that the fields are intended to contain the same information as each other or otherwise be related to each other. For example, the "Psychological Disorder" text field may be displayed far on the screen from the "Psychological Disorder" checkbox. Embodiments of the present invention enable actual and possible inconsistencies between corresponding free-form text elements and discrete data elements to be identified automatically, thereby increasing the likelihood that such inconsistencies will be eliminated. Such elimination assists in maintaining the validity of the discrete data elements the EMR, thereby increasing the utility of such data elements for purposes such as automatic clinical decision support.

A related advantage of embodiments of the present invention is that they may suggest actions to be performed to eliminate inconsistencies between free-form text elements and discrete data elements, but not perform such actions automatically. Instead, embodiments of the present invention may present such suggested actions to a user, such a physician, for approval, and only perform such suggested actions if and in response to approval from the user. Requiring user approval provides protection against errors by the suggestion module 312. Furthermore, in cases in which the suggestion module 312 suggests multiple actions which are inconsistent with each other as a result of failure of the free-form text input 310 to indicate a particular action with sufficient specificity, the user 306 must provide approval before any action may be taken. Although requiring user approval may cause inconsistencies to be eliminated more slowly and with more user effort than would be required by a fully automated system, requiring user approval balances such increases in efficiency with the benefits derived from performing automatically-suggested actions which are not justified by the underlying free-form text. Furthermore, embodiments of the present invention minimize the amount of effort required by the user 306, by enabling the user 306 to authorize the suggested actions 314 to be performed with a minimum of input (such as by clicking on the single "Apply Actions" button 256 in FIG. 2B), and by enabling the suggested actions 314 to be performed automatically in response to approval from the user 306.

Another advantage of embodiments of the present invention is that they may learn from the user 306's acceptance and rejection of suggested actions 314 to improve the suggestion module 312's future action suggestions. For example, each time the user 306 provides action response input 316 which accepts or rejects an action suggested by the suggested action output 314, the system 300 may store a record containing data representing one or more of the following:

the input 316 (e.g., whether the input 316 represents an acceptance or a rejection);
the suggested action 314 associated with the input 316;
any data that was used by the suggestion module 312 to generate the suggested action 314 (such as the free-form text input 310 and any values of discrete data elements in the EMR database 302 that were used to generate the suggested action 314); and
the discrete data element(s) suggested to be updated by the suggested action.

The system 300 may store such data for each of a plurality of suggested actions 314 and corresponding response inputs 316 from the user 306 (and possibly from other users). The system 300 may use any suitable machine learning technique to use such store data to modify the process by which the suggestion module 312 generates suggested actions 314 in the future. In general, if the system 300 determines that the stored data represents statistically significant evidence that a particular action should be suggested in the future in a particular context, then the system 300 may suggest that the particular action be performed in that particular context in the future. Similarly, if the system 300 determines that the stored data represents statistically significant evidence that a particular action should not be suggested in the future in a particular context, then the system 300 may not suggest that the particular action be performed in that particular context in the future. Such a technique enables the system 300 to improve the quality of its suggestions over time. For example, if the system 300 repeatedly suggests performing a particular action in a context in which the user 306 consistently rejects the suggestion, then the system 300 may use the stored data representing the user 306's consistent rejection of the suggested action to stop suggesting that action in the same context in the future.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions. As a particular example, the suggestion module 312 may be implemented solely in the EMR management module 304, be implemented solely in the computing device 308, be distributed across both the EMR management module 304 and the computing device 308, or in any other suitable manner to perform the functions disclosed herein.

The techniques disclosed herein are not limited to use in connection with any particular EMR system, or in connection with any particular EMR data. The particular EMR data elements disclosed herein are merely examples and do not constitute limitations of the present invention. Other EMR data elements include, but are not limited to, current and historical medication lists, allergies, and current and historical medical problems.

The techniques disclosed herein may be integrated into an EMR system and/or work by communicating with an EMR system. In the latter case, data may, for example, be transferred from the EMR system to a system implementing the techniques disclosed herein using an ASTM Continuity of Care Record (CCR) or an HL7 CDA Continuity of Care Document (CCD).

The techniques described above may be implemented, for example, in hardware, software tangibly embodied in a computer-readable medium, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in non-transitory signals in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

The invention claimed is:

1. A method for identifying, based on free-form text, a plurality of suggested actions for discrete data elements, and for performing at least one of the plurality of suggested actions, the method performed by at least one computer processor, the method comprising:
   (A) receiving the free-form text via a free-form text user interface element of a user interface;
   (B) identifying, based on the free-form text, a plurality of discrete data elements of a data structure;
   (C) identifying, based on the free-form text, the plurality of suggested actions, wherein the plurality of suggested actions comprises, for each discrete data element D in the plurality of discrete data elements of the data structure, a corresponding suggested action S comprising: storing a value in the discrete data element D, removing a current value of the discrete data element D, or performing a specified operation on a current value of the discrete data element D to produce a new value of the discrete data element D; and
   (D) performing the at least one of the plurality of suggested actions.

2. The method of claim 1, further comprising:
   (E) after identifying the plurality of suggested actions, providing output representing, for each discrete data element D in the plurality of discrete data elements of the data structure, the corresponding suggested action S.

3. The method of claim 2, wherein (E) comprises: generating visual and/or auditory output representing the corresponding suggested action S.

4. The method of claim 2, wherein (E) comprises modifying, for each discrete data element D in the plurality of discrete data elements of the data structure, a state of a corresponding discrete data user interface element in the user interface to cause the corresponding discrete data user interface element to reflect an outcome of performing the corresponding suggested action S.

5. The method of claim 2, wherein (E) comprises displaying, for each discrete data element D in the plurality of discrete data elements of the data structure, an instruction to modify a state of a discrete data user interface element corresponding to the discrete data element D in the user interface.

6. The method of claim 2, further comprising:
   (F) receiving a user input indicating user's acceptance of the at least one of the plurality of suggested actions, wherein the at least one of the plurality of suggested actions is performed in response to the receiving the user input.

7. The method of claim 6, wherein (F) comprises receiving a user input to modify a state of a discrete data user interface element in the user interface.

8. The method of claim 6, further comprising:
   (G) storing a record of the at least one of the plurality of suggested actions and the user input;

(H) repeating (A)-(F) at least once to produce a plurality of stored records of the plurality of suggested actions and a plurality of corresponding user inputs; and (I) modifying a process used to identify the plurality of suggested actions based on the plurality of stored records.

9. The method of claim 6, wherein the received user input includes one of: a different response input corresponding to each suggested action of the plurality of suggested actions, and a single response input corresponding to all of the plurality of suggested actions.

10. The method of claim 6, further comprising:
(G) displaying output representing outcome of performing the at least one of the plurality of suggested actions.

11. The method of claim 1, wherein the data structure comprises an electronic medical record.

12. The method of claim 1, wherein (C) comprises:
(C) (1) identifying a concept based on the free-form text;
(C) (2) determining, for each discrete data element D in the plurality of discrete data elements of the data structure, whether the concept is consistent with the discrete data element D; and
(C) (3) in response to determining that the concept is not consistent with the discrete data element D, identifying a suggested action, wherein the identified suggested action causes the discrete data element D to be consistent with the concept.

13. The method of claim 12, wherein (C) (1) comprises periodically submitting some or all of the free-form text to a natural language understanding (NLU) service that collects information from the free-form text to identify the concept.

14. The method of claim 1, further comprising:
(E) before receiving the free-form text, receiving a patient identifier, and
(F) before identifying the plurality of discrete data elements of the data structure, identifying the data structure associated with the patient identifier.

15. The method of claim 1, wherein the identifying the plurality of suggested actions is further based on data comprised in the plurality of discrete data elements of the data structure.

16. A non-transitory computer-readable medium comprising computer program instructions executable by at least one computer processor to perform a method, the method comprising:
(A) receiving free-form text via a free-form text user interface element of a user interface;
(B) identifying, based on the free-form text, a plurality of discrete data elements of a data structure;
(C) identifying, based on the free-form text, a plurality of suggested actions, wherein the plurality of suggested actions comprises, for each discrete data element D in the plurality of discrete data elements of the data structure, a corresponding suggested action S comprising: storing a value in the discrete data element D, removing a current value of the discrete data element D, or performing a specified operation on a current value of the discrete data element D to produce a new value of the discrete data element D; and
(D) performing at least one of the plurality of suggested actions.

17. The non-transitory computer-readable medium of claim 16, wherein the method further comprises:
(E) after identifying the plurality of suggested actions, providing output representing, for each discrete data element D in the plurality of discrete data elements of the data structure, the corresponding suggested action S.

18. The non-transitory computer-readable medium of claim 17, wherein (E) comprises: generating visual and/or auditory output representing the corresponding suggested action S.

19. The non-transitory computer-readable medium of claim 17, wherein (E) comprises modifying, for each discrete data element D in the plurality of discrete data elements of the data structure, a state of a corresponding discrete data user interface element in the user interface to cause the corresponding discrete data user interface element to reflect an outcome of performing the corresponding suggested action S.

20. The non-transitory computer-readable medium of claim 17, wherein (E) comprises displaying, for each discrete data element D in the plurality of discrete data elements of the data structure, an instruction to modify a state of a discrete data user interface element corresponding to the discrete data element D in the user interface.

21. The non-transitory computer-readable medium of claim 17, wherein the method further comprises:
(F) receiving a user input indicating user's acceptance of the at least one of the plurality of suggested actions, wherein the at least one of the plurality of suggested actions is performed in response to the receiving the user input.

22. The non-transitory computer-readable medium of claim 21, wherein (F) comprises receiving a user input to modify a state of a discrete data user interface element in the user interface.

23. The non-transitory computer-readable medium of claim 21, wherein the method further comprises:
(G) storing a record of the at least one of the plurality of suggested actions and the user input;
(H) repeating (A)-(F) at least once to produce a plurality of stored records of the plurality of suggested actions and a plurality of corresponding user inputs; and
(I) modifying a process used to identify the plurality of suggested actions based on the plurality of stored records.

24. The non-transitory computer-readable medium of claim 21, wherein the received user input includes one of: a different response input corresponding to each suggested action of the plurality of suggested actions, and a single response input corresponding to all of the plurality of suggested actions.

25. The non-transitory computer-readable medium of claim 21, wherein the method further comprises:
(G) displaying output representing outcome of performing the at least one of the plurality of suggested actions.

26. The non-transitory computer-readable medium of claim 16, wherein the data structure comprises an electronic medical record.

27. The non-transitory computer-readable medium of claim 16, wherein (C) comprises:
(C) (1) identifying a concept based on the free-form text;
(C) (2) determining, for each discrete data element D in the plurality of discrete data elements of the data structure, whether the concept is consistent with the discrete data element D; and
(C) (3) in response to determining that the concept is not consistent with the discrete data element D, identifying a suggested action, wherein the identified suggested action causes the discrete data element D to be consistent with the concept.

28. The non-transitory computer-readable medium of claim 27, wherein (C) (1) comprises periodically submitting some or all of the free-form text to a natural language understanding (NLU) service that collects information from the free-form text to identify the concept.

29. The non-transitory computer-readable medium of claim 16, wherein method further comprises:
- (E) before receiving the free-form text, receiving a patient identifier, and
- (F) before identifying the plurality of discrete data elements of the data structure, identifying the data structure associated with the patient identifier.

30. The non-transitory computer-readable medium of claim 16, wherein the identifying the plurality of suggested actions is further based on data comprised in the plurality of discrete data elements of the data structure.

\* \* \* \* \*